United States Patent [19]

Schaafsma et al.

[11] 4,291,170

[45] Sep. 22, 1981

[54] PREPARATION OF DELTA-KETO-ESTERS

[75] Inventors: Sijbrandus E. Schaafsma, Beek;
Johannes H. A. Hofman, Maastricht;
Johannes E. L. Claassens, Heerlen,
all of Netherlands

[73] Assignee: Stamicarbon, B.V., Geleen,
Netherlands

[21] Appl. No.: 798,888

[22] Filed: May 20, 1977

Related U.S. Application Data

[63] Continuation of Ser. No. 413,436, Nov. 7, 1973, abandoned.

[30] Foreign Application Priority Data

Nov. 11, 1972 [NL] Netherlands ............... 7215305

[51] Int. Cl.$^3$ ............... C07C 67/313

[52] U.S. Cl. ............... 560/126; 560/121; 560/174

[58] Field of Search ............... 560/121, 126, 174

[56] References Cited

PUBLICATIONS

House, Modern Synthetic Reactions, pp. 595–615 (1972).

*Primary Examiner*—Robert Gerstl
*Attorney, Agent, or Firm*—Cushman, Darby & Cushman

[57] ABSTRACT

Delta-keto-esters such as 4-oxopentane-1-carboxylic acid methyl ester and the like, are prepared in the presence of a primary amine, a Schiff base, or both, by reacting a ketone having at least one hydrogen atom in the alpha position and an alpha-beta unsaturated carboxylic acid ester in the presence of an acid according to the disclosed invention.

9 Claims, No Drawings

PREPARATION OF DELTA-KETO-ESTERS

This is a continuation of application Ser. No. 413,436 filed Nov. 7, 1973.

The present invention relates to a process for preparing delta-keto-esters by liquid-phase reaction of an alpha-beta unsaturated carboxylic acid ester and a ketone, in which at least one hydrogen atom occurs in an alpha place in the ketone.

BACKGROUND OF THE INVENTION

It has been proposed in Comptes Rendus 248, 1959, pages 1533-1535 for the addition reaction of a ketone of this kind with an acrylic acid ester to be conducted in the presence of an alkaline catalyst, such as sodium amide or potassium ethylate. However, in that case the ester group has such an adverse influence on the reactivity of the double bond in the acrylic acid ester that for most ketones the addition takes place at a very low efficiency. In the addition of methyl acrylate to methyl benzyl ketone, however, an efficiency of 82% is reached, which, probably, should be attributed to the activation of the alpha-hydrogen-atom, which is not only activated by the carbonyl group but also by the benzyl group.

DETAILED DESCRIPTION OF THE INVENTION

We have now found a process in which this addition can also be accomplished at an attractive efficiency if the alpha-hydrogen-atom is activated by the carbonyl group exclusively, and in which, in addition to esters of acrylic acid, other alpha-beta unsaturated carboxylic acid esters may also be added. The process according to the present invention is characterized in that the reaction is carried out with the aid of a primary amine, a Schiff base, or both, as catalysts, and that a reaction mixture is used containing an acid compound. As used herein, the terms primary amine and Schiff base also comprise compounds in which, by the side of the primary amino group, respectively the N-substituted imine group, another functional group is present, for instance an amino acid.

In the addition reaction according to the present invention numerous ketones may be applied as starting product, and generally containing from 3 to 10 carbon atoms, preferably 3 to 7 carbon atoms, and include acetone, methyl ethyl ketone, methyl propyl ketone, diethyl ketone, methyl isopropyl ketone, cyclopentanone, cyclohexanone, 2-methyl cyclohexanone and 4-methyl cyclohexanone.

Various alpha-beta unsaturated carboxylic acid esters may be used, derived from acids having from 3 to 8 carbon atoms, preferably 3 to 5 carbon atoms in the process according to the present invention; however in practice the methyl and ethyl esters of acrylic acid, methacrylic acid and crotonic acid are of the most commercial importance.

As previously indicated, the present invention is characterized by the use of a primary amine, Schiff base, or both, as a catalyst. We prefer to use a primary amine containing from 1 to 6 carbon atoms in the alkyl group which is either straight-chained or branched, preferably branched. Specific examples include methyl amine, ethyl amine, n-propyl amine, isopropyl amine, n-butyl amine, isobutyl amine, secondary butyl amine, secondary pentyl amine, n-hexyl amine, cyclopentyl amine, cyclohexyl amine, hexamethylene diamine, $\epsilon$-amino caproic acid and the Schiff bases of a ketone or aldehyde with one of the primary amines mentioned above. Extremely suitable catalysts are isopropyl amine, cyclohexyl amine and the Schiff bases derived from these amines and the ketone to be converted, and hence are the most preferred catalysts for use in the process disclosed. The catalyst quantity may be of course varied but will generally be in the order of 0.01 to 0.25 mole of catalyst for every mole of carboxylic acid ester.

Another characterizing feature of the present invention is that an acid or acid compound is employed which acid or acid compound is capable of decreasing the pH value of a neutral aqueous solution and/or which contains a functional acid group. In principle, nearly any acid may be used so long as it is non-reactive with the reactants and products.

Suitable acids and acid compounds include acetic acid, adipic acid, benzoic acid, phenol, caproic acid and the inorganic mineral acids such as hydrochloric acid, phosphoric acid and sulphuric acid. Ammonium chloride may also be used. Only a minor amount of an acid compound, for instance 0.01-0.5 mole per mole of catalyst, is necessary for the reaction according to the present invention. If the catalyst should also contain an acid group, as in the case, for instance of $\epsilon$-amino caproic acid, the use of an additional acid compound is not required.

Depending on the ratio between the ketone and the carboxylic acid ester, di-addition product can be formed concurrently with the mono-addition product, unless only one hydrogen atom is present in the alpha position on the ketone. If the formation of di-addition product is possible, the formation of mono-addition product can be favored by using a ketone to carboxylic acid ester ratio greater than 1:1, otherwise ketone:carboxylic acid ester ratios may generally vary from about 1:4 to about 10:1.

The process according to the present invention is preferably conducted at a temperature between about 75 and 250° C., for at a temperature in excess of 250° C. the efficiency is influenced adversely by side-reactions, while on the other hand at a temperature below 75° C., the reaction proceeds too slowly for practical efficiency. The pressure is not critical and may be varied within rather wide limits. In combination with the temperature, the pressure should, of course, be selected such that the reaction is conducted in the liquid phase, whether or not a solvent or a distributing agent is employed. However, if a solvent or a distributing agent (diluent) is used, any inert solvent or distributing agent inert to the reactants, catalyst(s) and products will be suitable in principle. Illustrative materials include benzene, toluene, cyclohexane, n-hexane and chlorobenzene. The use of a solvent or diluent is optional as it is not required for the process.

In the process according to the present invention the ketone, the ester, or both, can be wholly or partly converted depending in part on the reaction conditions. After the desired conversion has been reached, the reaction mixture may be separated into its various components by distillation, in which, beside the desired product, a fraction can be obtained which is rich in catalyst and which can be reused and recirculated.

Delta-keto-acid esters of the present invention are known compounds and are useful in a number of different applications. For example, they may be used as starting products for the preparation of other valuable products. For instance, if in the process according to the present invention one starts from a cyclohexanone, optionally alkyl substituted, a delta-keto-acid ester is obtained which can be converted, according to U.S. Pat. No. 3,442,910, the disclosure of which is hereby incorporated by reference, into the correspondingly substituted dihydrocoumarin, which is useful to the fragrances industry. Another use is in the preparation of dihydroresorcinol, optionally substituted, from the delta-keto-acid ester obtained from an alphatic ketone; see A. N. Kost and L. G. Ovseneva, Zhurnal Obschchei Khimii, volume 32, page 3983. Other uses will be apparent to the skilled chemist.

The process according to the invention will be in more detail in the following examples in which all parts and described percentages are by weight unless otherwise indicated.

EXAMPLE 1

Preparation of 4-oxopentane-1-carboxylic acid methyl ester

Acetone (1740 g), methyl acrylate (645 g), isopropyl amine (25 g) and benzoic acid (2.1 g) are charged into a 5 litter autoclave. The mixture in the autoclave is then heated to 160° C. at autogenic pressure and maintained at this temperature for 2 hours. The reaction mixture is then cooled rapidly and transferred to a distillation flask. By distillation at atmospheric pressure the mixture is separated into 2011 g of distillate boiling below 125° C. and 380 g of residue. According to gaschromatographic analysis the distillate contains 1580 g of acetone and 377 g of methyl acrylate.

According to gaschromatographic analysis the residue contains 323 g of the methyl ester of 4-oxopentane-1-carboxylic acid.

By fractional distillation a main fraction of 312.7 g having a boiling point of 92°–93° C. at 10 mm Hg is obtained which, according to gaschromatographic and spectrometric analysis, consists of pure 4-oxopentane-1-carboxylic acid methyl ester (refractive index $20/n_D = 1.4288$).

41.5% of the total quantity of methyl acrylate has been converted and calculated in relation to the amount of converted acetone, the efficiency amounts to 81%, and to 72% referred to the quantity of converted methyl acrylate.

EXAMPLE 2

Preparation of 4-oxopentane-1-carboxylic acid methyl ester

Acetone (348 g), methyl acrylate (172 g), isopropyl amine (4 g) and benzoic acid (0.3 g) are charged into a 1 liter autoclave. The molar ratio of acetone to methyl acrylate is 3:1. The mixture is then heated for 2 hours at 175° C. at autogenic pressure, then cooled rapidly and separated by fractionating distillation at reduced pressure into the following fractions:

(a) Fraction having a boiling point below 92° C. at 10 mm Hg weight 392.2 g.

(b) Fraction having a boiling range of 90°–96° C. at 10 mm Hg weight 73.9 g.

(c) Fraction having a boiling range of 96°–168° C. at 10 mm Hg weight 1.8 g.

(d) Fraction having a boiling range of 168°–175° C. at 10 mm Hg weight 21.8 g.

The fractions so obtained were then analyzed gaschromatographically and spectrometrically, indicating the following results:

Fraction (a) contains acetone, methyl acrylate, N-isopropyl acetonimine and (2-carbomethoxyethyl)-isopropyl amine. According to the quantitative analysis the fraction contains 25.8% by weight of methyl acrylate. Fraction (b) contains 95.1% by weight of 4-oxopentane-1-carboxylic acid methyl ester. Fraction (d) consists of a mixture of diesters composed of 70% by weight of dimethyl ester of 3-acetyl-pentane dicarboxylic acid-1.5 and 21% by weight of dimethyl ester of 4-oxoheptane dicarboxylic acid-1.7.

41% of the total quantity of methyl acrylate has been converted. Calculated with respect to converted methyl acrylate the efficiency in 4-oxopentane-1-carboxylic acid methyl ester amounts to 59%, and in di-addition products to 21%.

EXAMPLE 3

Preparator of 4-oxopentane-1-carboxylic acid methyl ester

Acetone (1540 g), methyl acrylate (430 g) and benzoic acid (2 g) are charged into a 5 liter autoclave and heated to 165° C. at autogenic pressure. Subsequently, over a period of about 5 minutes a solution consisting of isopropyl amine (24 g), benzoic acid (0.5 g) and acetone (200 g) is pumped into the autoclave, the resulting mixture being kept at 165° C. for 3 hours. The reaction mixture is cooled and transferred to a distillation flask.

By distillation at atmospheric pressure the reaction mixture is separated into 1801 g of distillate, boiling below 125° C., and 379.3 g of residue.

According to gaschromatographic analysis the distillate contains 1581 g of acetone and 207 g of methyl acrylate, the residue containing 302 g of methyl ester of 4-oxopentane-1-carboxylic acid.

52% of the total amount of methyl acrylate has been converted. Calculated with respect to the quantity of converted acetone the efficiency amounts to 76%, and to 81% referred to the quantity of methyl acrylate.

EXAMPLE 4

Preparation of 3-methyl-4-oxo-pentane-1-carboxylic acid ethyl ester

Methyl ethyl ketone (360 g), ethyl acrylate (125 g), isopropyl amine (4 g) and benzoic acid (0.4 g) are charged into a 1 liter autoclave. The mixture is heated for 3 hours at 170° C. at autogenic pressure. The molar ratio of methyl ethyl ketone to ethyl acrylate was 4:1. Subsequently, the reaction mixture is cooled, transferred to a distillation flask, and separated by distillation into:

(a) Fraction boiling below 98° C. at 9 mm Hg, the weight being 401.2 g.

(b) Fraction having a boiling range of 98°–102° C. at 9 mm Hg, the weight being 53.9 g.

(c) Residue having a weight of 28.9 g.

Fraction (a) contains 322 g of methyl ethyl ketone and 73.8 g of ethyl acrylate.

Fraction (b) contains 95% by weight of ethyl ester of 3-methyl-4-oxopentane-1-carboxylic acid and 2% by weight of ethyl ester of 4-oxo-hexane-1-carboxylic acid. 41% of the total amount of ethyl acrylate has been converted. The efficiency in ethyl ester of 3-methyl-4-oxo-pentane-1-carboxylic acid amounts to 56% referred to the quantity of converted methyl ethyl ketone, and to 58% referred to the quantity of converted ethyl acrylate.

EXAMPLE 5

Preparation of methyl 3-(2-oxocyclohexyl) propionate

Cyclohexanone (147.0 g), methyl acrylate (86.0 g), cyclohexyl amine (5.0 g) and benzoic acid (0.5 g) are charged into a 1 liter flask fitted with a stirrer and a refux cooler. The mixture is heated to 100° C. with stirring. Subsequently, heating is continued such that the mixture keeps boiling gently. After 20 hours, the temperature in the flask has risen to 155° C. The reaction mixture is then separated by distillation into a fraction boiling below 140° C. at 13 mm Hg (weight 56.1 g), a second fraction having a boiling range of 140° to 144° C. at 13 mm Hg (weight 157.0 g) and a higher-boiling residue (weight 24.9 g).

According to gaschromatographic analysis the first distillate fraction contains 52.3 of cyclohexanone and 1.2 g of methyl acrylate. The second distillate fraction contains 154.9 of methyl 3-(2-oxocyclohexyl)-propionate product.

The efficiency in methyl-3-(2-oxocyclohexyl)-propionate amounts, therefore, to 85% calculated on the quantity of methyl acrylate converted, and to 87% referred to the quantity of cyclohexanone converted.

EXAMPLE 6

Preparation of methyl-3-(1-methyl-2-oxocyclohexyl)propionate and methyl-3-(3-methyl-2-oxocyclohexyl)propionate In the manner of Example 5, 2-methyl cyclohexanone (168 g) is reacted with methyl acrylate (86 g) in the presence of cyclohexyl amine (5 g) and benzoic acid (0.5 g).

The reaction mixture so obtained is separated by distillation into a fraction boiling below 73° C. at 0.1 mm Hg (weight 87.0 g), a second fraction having a boiling range of 73°–76° C. at 0.1 mm Hg (weight 132.5 g) and a higher-boiling residue (weight 36.1 g).

The first distillate fraction contains 72.8 g of 2-methyl cyclohexanone and 4.3 g of methyl acrylate.

The second distillate fraction contains 89% by weight by methyl-3-(1-methyl-2-oxocyclohexyl)-propionate and 9% by weight of methyl-3-(3-methyl-2-oxocyclohexyl)-propionate The efficiency in methyl-3-(1-methyl-2-oxocyclohexyl)-propionate amounts to 63% calculated on the methyl acrylate converted, and 70% calculated on the 2-methyl cyclohexanone converted.

The efficiency in methyl-3-(3-methyl-2-oxocyclohexyl)-propionate amounts to 6% calculated on the methyl acrylate converted, and 7% calculated on the 2-methyl cyclohexanone converted.

EXAMPLE 7

Preparation of methyl-3-(2-oxocyclohexyl)-propionate

Cyclohexanone (4.9 g), methyl acrylate (4.3 g), 2-butyl amine (0.3 g) and benzoic acid (0.03 g) are reacted together in a stainless steel tube having a capacity of 15 ml. The tube is sealed and heated at a temperature of 160° C. for 3 hours.

The tube is then cooled rapidly and the reaction mixture (9.5 g) analyzed gaschromatographically.

The mixture contains 8.9% by weight of cyclohexanone, 21.1% by weight of methyl acrylate and 76.0% by weight of methyl-3-(2-oxocyclohexyl)-propionate. The methyl acrylate conversion amounts therefore to 95%. The efficiency in methyl-3-(2-oxocyclohexyl)-propionate amounts to 95% calculated on the quantity of cyclohexanone converted, and to 83% calculated on the quantity of methyl acrylate converted.

EXAMPLES 8–14

Preparaton of 4-oxopentane-1-carboxylic acid methyl ester

In a number of stainless steel tubes having a capacity of 15 ml a mixture of acetone (5.8 g, 0.1 mole) and methyl acrylate (2.15 g, 0.025 mole) is heated at 170° C. for 2 hours, together with a primary amine (5 mol.-% referred to methyl acrylate) and an acid (0.25 mol.-% referred to methyl acrylate) both as identified in the following table.

Subsequently, the tubes are cooled rapidly, following which the contents of the tubes is analyzed gaschromatographically, and the conversion of the methyl acrylate, as well as the efficiency in the methyl ester of 4-oxopentane-1-carboxylic acid product, referred to the converted methyl acrylate, is determined.

The results of these experiments are given in the following table:

| Example No. | 8 | 9 | 10 | 11 | 12 | 13 | 14 |
|---|---|---|---|---|---|---|---|
| catalyst | iso-propyl amine | 2-butyl-amine | n-hexyl-amine | cyclo-hexyl amine | iso-propyl amine | ani-line | n-iso-propyl acetone imine |
| acid | benzoic acid | benzoic acid | benzoic acid | benzoic acid | acetic acid | capro-ic acid | benzoic acid |
| conversion of methyl acrylate (%) | 61.6 | 57.5 | 64.3 | 61.2 | 34.6 | 5.8 | 44.2% |
| efficiency referred to converted methyl acrylate | 68.0 | 57.7 | 48.1 | 71.1 | 48.7 | 77.4 | 55.8% |

EXAMPLE 15

Preparation of 2-methyl-4-oxo-pentane-1-carboxylic acid

Acetone (232 g), methyl crotonate (100 g), isopropyl amine (3 g) and benzoic acid (0.3 g) are collected. The mixture is heated at 180° C. for 3 hours at autogenic pressure. Subsequently, the reaction mixture is cooled, transferred to a distillation flask, and separated by distillation into:

(a) Fraction boiling below 95° C. at 10 mm Hg, the weight being 300.2 g.

(b) Fraction having a boiling range of 95°–100° C. at 10 mm Hg, the weight being 21.5 g.

(c) Residue having a weight of 7.0 g.

Fraction (a) contains 216.0 of acetone and 79.9 of methyl crotonate.

Fraction (b) contains 19.8 g of methyl ester of 2-methyl-4-oxo-pentane-1-carboxylic acid.

20% of the total amount of methyl crotonate was converted. The efficiency in methyl ester of 2-methyl-4-oxo-pentane-1-carboxylic acid amounted to 45% calculated on the quantity of acetone converted, and to 62% calculated on the quantity of methyl crotonate converted.

What is claimed is:

1. Process for the preparation of a delta-keto-ester comprising reacting together in the liquid phase at a temperature of about 75° to 250° C. of an ester of an alpha-beta unsaturated carboxylic acid derived from acids having from 3 to 8 carbon atoms with a ketone having 3 to 10 carbon atoms, provided that said ketone has at least one hydrogen atom in the alpha position thereof, in the presence of primary amine containing from 1 to 6 carbon atoms, a Schiff base of said amine, or both, and an acid compound to form the corresponding delta-keto-ester.

2. The process according to claim 1 wherein 0.01–0.25 mole of catalyst is applied per mole of carboxylic acid ester.

3. The process according to claim 1 wherein said catalyst is isopropyl amine, cyclohexyl amine, or a Schiff base formed from said ketone and from one of said primary amines.

4. The process according to claim 1 wherein said alpha-beta unsaturated carboxylic acid is acrylic acid, methacrylic acid or crotonic acid.

5. The process according to claim 1 wherein said ketone is acetone, methyl ethyl ketone, methyl propyl ketone, diethyl ketone, methyl isopropyl ketone, cyclopentanone, cyclohexanone, 2-methyl cyclohexanone or 4-methyl cyclohexanone.

6. The process according to claim 1 wherein the ratio of said ketone to said carboxylic acid ester is greater than 1:1.

7. The process of claim 1, wherein said primary amine, said Schiff base or said both and said acid compound are present in a catalytic amount effective to form said delta-keto-ester.

8. Process for the preparation of a delta-keto-ester comprising reacting together in the liquid phase at a temperature of about 75° to 250° C. (1) an ester of an alpha-beta unsaturated carboxylic acid derived from acids having from 3 to 8 carbon atoms with (2) an aliphatic ketone having from 3 to 10 carbon atoms, provided that said ketone has at least one hydrogen atom in the alpha position thereof, in the presence of a primary amine containing from 1 to 6 carbon atoms, a Schiff base of said amine, or both, and an acid compound to form the corresponding delta-keto-ester.

9. Process for the preparation of a delta-keto-ester comprising reacting together in the liquid phase at a temperature of about 75° to 250° C. of an ester of an alpha-beta unsaturated carboxylic acid derived from acids having from 3 to 8 carbon atoms with cyclohexanone in the presence of a primary amine containing from 1 to 6 atoms, a Schiff base of said amine, or both, and an acid compound to form the corresponding delta-keto-ester.

* * * * *